(12) United States Patent
Begg (10) Patent No.: US 11,497,540 B2
(45) Date of Patent: Nov. 15, 2022

(54) ELECTROSURGICAL FALLOPIAN TUBE SEALING DEVICES WITH SUCTION AND METHODS OF USE THEREOF

(71) Applicant: Covidien LP, Mansfield, MA (US)

(72) Inventor: Nikolai D. Begg, Wellesley, MA (US)

(73) Assignee: COVIDIEN LP, Mansfield, MA (US)

( * ) Notice: Subject to any disclaimer, the term of this patent is extended or adjusted under 35 U.S.C. 154(b) by 217 days.

(21) Appl. No.: 16/737,399

(22) Filed: Jan. 8, 2020

(65) Prior Publication Data

US 2020/0214755 A1    Jul. 9, 2020

Related U.S. Application Data

(60) Provisional application No. 62/790,064, filed on Jan. 9, 2019.

(51) Int. Cl.
*A61B 18/00* (2006.01)
*A61B 17/42* (2006.01)

(52) U.S. Cl.
CPC ...... *A61B 18/00* (2013.01); *A61B 2017/4233* (2013.01); *A61B 2018/00083* (2013.01);
(Continued)

(58) Field of Classification Search
CPC ............ A61B 18/00; A61B 2017/4233; A61B 2018/00083; A61B 2018/00559;
(Continued)

(56) References Cited

U.S. PATENT DOCUMENTS 2,054,149 A    9/1936  Wappler
4,493,320 A    1/1985  Treat
(Continued)

FOREIGN PATENT DOCUMENTS

CA    2104423 A1    2/1994
DE    2415263 A1    10/1975
(Continued)

OTHER PUBLICATIONS

Int'l Search Report PCT/US2020/012716 dated May 7, 2020.
(Continued)

*Primary Examiner* — Linda C Dvorak
*Assistant Examiner* — Mystee Nguyen Delgado
(74) *Attorney, Agent, or Firm* — Carter, DeLuca & Farrell LLP (57) ABSTRACT

An electrosurgical device includes an elongated shaft, an active electrode, and a return electrode. The elongated shaft has an end effector that is operably engaged with a distal portion thereof and a channel defined therethrough. The distal portion of the elongated shaft includes a distal tip that is configured to provide suction from a suction surface to the distal tip through the channel. The end effector may include a flare a proximal end thereof. The active electrode is positioned adjacent the distal tip of the elongated shaft and is configured to deliver electrosurgical energy to tissue. The return electrode is positioned on an outer surface of the end effector proximal of the active electrode. The return electrode is configured to provide a return path for the electrosurgical energy.

16 Claims, 5 Drawing Sheets

(52) U.S. Cl.
CPC ............. *A61B 2018/00559* (2013.01); *A61B 2218/007* (2013.01)

(58) Field of Classification Search
CPC ...... A61B 2218/007; A61B 2018/0063; A61B 2018/162; A61B 18/1485; A61B 2018/0231; A61B 18/082; A61B 2018/00315
See application file for complete search history.

(56) References Cited

U.S. PATENT DOCUMENTS

| | | | |
|---|---|---|---|
| 4,503,855 A | 3/1985 | Maslanka | |
| 5,078,716 A | 1/1992 | Doll | |
| 5,520,698 A | 5/1996 | Koh | |
| 5,556,396 A | 9/1996 | Cohen et al. | |
| 5,558,672 A | 9/1996 | Edwards et al. | |
| 5,562,720 A | 10/1996 | Stern et al. | |
| 5,643,285 A | 7/1997 | Rowden et al. | |
| 5,709,224 A | 1/1998 | Behl et al. | |
| 5,840,077 A | 11/1998 | Rowden et al. | |
| 5,902,300 A | 5/1999 | Hahnen et al. | |
| 6,221,039 B1 | 4/2001 | Durgin et al. | |
| 6,258,088 B1* | 7/2001 | Tzonev .............. A61B 18/1402 606/49 |
| 6,485,486 B1 | 11/2002 | Trembly et al. | |
| 6,508,815 B1 | 1/2003 | Strul et al. | |
| 6,517,538 B1 | 2/2003 | Jacob et al. | |
| 6,896,682 B1 | 5/2005 | McClellan et al. | |
| 6,972,017 B2 | 12/2005 | Smith et al. | |
| 7,135,018 B2 | 11/2006 | Ryan et al. | |
| 8,016,827 B2 | 9/2011 | Chojin | |
| 8,114,122 B2 | 2/2012 | Nau, Jr. | |
| 8,142,473 B2 | 3/2012 | Cunningham | |
| 8,162,973 B2 | 4/2012 | Cunningham | |
| 8,197,479 B2 | 6/2012 | Olson et al. | |
| 8,226,650 B2 | 7/2012 | Kerr | |
| 8,251,994 B2 | 8/2012 | McKenna et al. | |
| 8,257,387 B2 | 9/2012 | Cunningham | |
| 8,747,413 B2* | 6/2014 | Dycus .................. A61B 18/14 606/135 |
| 9,931,160 B2 | 4/2018 | Jenkins | |
| 2003/0014050 A1 | 1/2003 | Sharkey et al. | |
| 2005/0125006 A1 | 6/2005 | Nady | |
| 2007/0078459 A1 | 4/2007 | Johnson et al. | |
| 2007/0142844 A1 | 6/2007 | Kotmel et al. | |
| 2007/0198011 A1 | 8/2007 | Sugita | |
| 2007/0213706 A1 | 9/2007 | Dumbauld et al. | |
| 2008/0125705 A1* | 5/2008 | Sato .................. A61B 18/1492 604/93.01 |
| 2008/0245371 A1 | 10/2008 | Gruber | |
| 2009/0182324 A1 | 7/2009 | Kurtulus | |
| 2009/0198233 A1 | 8/2009 | Chojin | |
| 2009/0209957 A1 | 8/2009 | Schmaltz et al. | |
| 2009/0209960 A1 | 8/2009 | Chojin | |
| 2009/0234354 A1 | 9/2009 | Johnson et al. | |
| 2009/0248021 A1 | 10/2009 | McKenna | |
| 2010/0016857 A1 | 1/2010 | McKenna et al. | |
| 2010/0036375 A1 | 2/2010 | Regadas | |
| 2010/0042140 A1 | 2/2010 | Cunningham | |
| 2010/0042143 A1 | 2/2010 | Cunningham | |
| 2010/0049187 A1 | 2/2010 | Carlton et al. | |
| 2010/0057081 A1 | 3/2010 | Hanna | |
| 2010/0057082 A1 | 3/2010 | Hanna | |
| 2010/0057083 A1 | 3/2010 | Hanna | |
| 2010/0057084 A1 | 3/2010 | Hanna | |
| 2010/0063500 A1 | 3/2010 | Muszala | |
| 2010/0069903 A1 | 3/2010 | Allen, IV et al. | |
| 2010/0069904 A1 | 3/2010 | Cunningham | |
| 2010/0069953 A1 | 3/2010 | Cunningham et al. | |
| 2010/0076427 A1 | 3/2010 | Heard | |
| 2010/0076430 A1 | 3/2010 | Romero | |
| 2010/0076431 A1 | 3/2010 | Allen, IV | |
| 2010/0076432 A1 | 3/2010 | Horner | |
| 2010/0087816 A1 | 4/2010 | Roy | |
| 2010/0094285 A1 | 4/2010 | Arts et al. | |
| 2010/0094287 A1 | 4/2010 | Cunningham et al. | |
| 2010/0100122 A1 | 4/2010 | Hinton | |
| 2010/0106156 A1 | 4/2010 | Laufer et al. | |
| 2010/0179545 A1 | 7/2010 | Twomey et al. | |
| 2010/0179546 A1 | 7/2010 | Cunningham | |
| 2010/0179547 A1 | 7/2010 | Cunningham et al. | |
| 2010/0256635 A1 | 10/2010 | McKenna et al. | |
| 2010/0280524 A1 | 11/2010 | Lopez Zepeda | |
| 2016/0331450 A1* | 11/2016 | Ben-Ezra .............. A61M 19/00 |
| 2017/0000550 A1* | 1/2017 | Marion .............. A61B 18/1206 |

FOREIGN PATENT DOCUMENTS

| | | |
|---|---|---|
| DE | 02514501 A1 | 10/1976 |
| DE | 2627679 A1 | 1/1977 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| EP | 0467501 A1 | 1/1992 |
| EP | 1159926 A2 | 3/2003 |
| EP | 1769766 A1 | 4/2007 |
| EP | 1439793 B1 | 5/2007 |
| GB | 623316 A | 5/1949 |
| GB | 1490585 A | 11/1977 |
| GB | 2213416 A | 8/1989 |
| GB | 2214430 A | 9/1989 |
| JP | 61501068 A | 5/1986 |
| JP | 65502328 | 3/1992 |
| JP | 55106 | 1/1993 |
| JP | 540112 | 2/1993 |
| JP | 06343644 | 12/1994 |
| JP | 07265328 | 10/1995 |
| JP | 08056955 | 3/1996 |
| JP | 08252263 A | 10/1996 |
| JP | 09010223 | 1/1997 |
| JP | 11244298 | 9/1999 |
| JP | 2000342599 A | 12/2000 |
| JP | 2000350732 A | 12/2000 |
| JP | 2001008944 | 1/2001 |
| JP | 2001029356 | 2/2001 |
| JP | 2001128990 A | 5/2001 |
| SU | 401367 A1 | 10/1973 |
| WO | 9321845 A1 | 11/1993 |
| WO | 9613218 A1 | 5/1996 |

OTHER PUBLICATIONS

U.S. Appl. No. 12/336,970, filed Dec. 17, 2008, Sremcich.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.

(56) References Cited

OTHER PUBLICATIONS

Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Carus et al., "Initial Experience With the LigaSure Vessel Sealing System in Abdominal Surgery" Innovations That Work,Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report" Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Intl Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.

(56) References Cited

OTHER PUBLICATIONS

Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Extended European Search Report for Application No. 20738771.3 dated Aug. 30, 2022.

* cited by examiner

ELECTROSURGICAL FALLOPIAN TUBE SEALING DEVICES WITH SUCTION AND METHODS OF USE THEREOF

CROSS REFERENCE TO RELATED APPLICATIONS

This application claims the benefit of and priority to U.S. Provisional Patent Application No. 62/790,064 filed Jan. 9, 2019. The entire content of which is incorporated herein by reference.

BACKGROUND

1. Technical Field

The present disclosure relates to surgical devices and, more specifically, electrosurgical devices for sealing fallopian tubes including suction.

2. Discussion of Related Art

Generally, there are two approaches for permanently sterilizing women. One method involves an abdominal approach, e.g., salpingectomy, tubal litigation, which can be done as an invasive or a minimally-invasive procedure both of which require general anesthesia. Another method involves a hysteroscopic approach for fallopian tubal occlusion which includes the placement of permanent implants into the fallopian tubes to prevent fertilization of ovum. The hysteroscopic approach may be completed in a medical office without requiring general anesthesia but also requires foreign materials to be left within the body cavity.

SUMMARY

This disclosure relates generally to electrosurgical devices that can be used through a hysteroscopic approach to permanently seal fallopian tubes without leaving foreign materials within the body cavity. In addition, the electrosurgical devices disclosed herein may be used in a medical office without the need for general anesthesia.

In an aspect of the present disclosure, an electrosurgical device includes an elongated shaft, an active electrode, and a return electrode. The elongated shaft has an end effector that is operably engaged with a distal portion thereof and a channel defined therethrough. The distal portion of the elongated shaft includes a distal tip that is configured to provide suction from a suction source to the distal tip through the channel. The end effector may include a flare at a proximal end thereof. The active electrode is positioned adjacent the distal tip of the elongated shaft and is configured to deliver electrosurgical energy to tissue. The return electrode is positioned on an outer surface of the end effector proximal of the active electrode. The return electrode is configured to provide a return path for the electrosurgical energy.

In aspects, the electrosurgical device includes an insulator disposed about the elongated shaft between the active and return electrodes.

In some aspects, the electrosurgical device includes a flare that radially expands as the flare extends proximally from the distal tip of the elongated shaft. The return electrode may be disposed on a proximal outer edge of the flare.

In certain aspects, the electrosurgical device includes a handle that is operably engaged to a proximal portion of the elongated shaft. The handle may include a vacuum source that is disposed therein. The vacuum source may be in communication with the channel of the elongated shaft and may be configured to provide suction through the distal tip of the elongated shaft.

In particular aspects, the elongated shaft is flexible. The channel of the elongated shaft may be curved between a proximal portion and a distal portion of the elongated shaft.

In another aspect of the present disclosure, the electrosurgical system includes an electrosurgical device, a vacuum source, and an electrosurgical generator. The electrosurgical device includes an elongated shaft, an active electrode, and a return electrode. The elongated shaft has a distal portion and a channel defined therethrough. The distal portion has a distal tip. The active electrode is positioned adjacent the distal tip of the elongated shaft and is configured to deliver electrosurgical energy to tissue. The return electrode is positioned on an outer surface of the distal portion of the elongated shaft proximal of the active electrode. The return electrode is configured to provide a return path for the electrosurgical energy. The vacuum source is in communication with the channel and is configured to provide suction to the distal tip of the elongated shaft. The electrosurgical generator is in electrical communication with the active electrode and the return electrode.

In aspects, the electrosurgical system includes a first control in communication with the vacuum source and is configured to control activation of the vacuum source and a second control in communication with the electrosurgical generator and is configured to control activation of the electrosurgical generator. The first and second controls may be operably engaged to one another as a single two-stage switch. The electrosurgical device may include a handle that is operably engaged with a proximal portion of the elongated shaft. At least one of the first or second controls may be disposed on the handle. At least one of the first or second controls may be a foot pedal.

In some aspects, the electrosurgical system includes a guide tube that has a channel defined therethrough and a distal end configured to position the electrosurgical device within a patient.

In another aspect of the present disclosure, a method of sealing a fallopian tube includes inserting a distal portion of an electrosurgical device into a fallopian tube using a hysteroscopic approach, applying suction, and delivering electrosurgical energy to tissue. Applying the suction includes applying the suction through a distal tip of the electrosurgical device to collapse the fallopian tube adjacent the distal tip. Delivering the electrosurgical energy to the tissue includes delivering the electrosurgical energy to the tissue from an active electrode disposed adjacent the distal tip of the electrosurgical device such that the electrosurgical energy is returned through a return electrode that is positioned on an outer surface of the distal portion proximal of the active electrode while applying the suction through the distal tip such that the tissue of the fallopian tubes is electrosurgically sealed adjacent the distal tip.

In aspects, applying suction through the distal tip of the electrosurgical device includes activating a vacuum source that is in communication with a channel that is defined within and extends through the electrosurgical device. Delivering the electrosurgical energy to the tissue may include activating an electrosurgical generator to supply energy to the active electrode.

In some aspects, the method includes withdrawing the distal portion of the electrosurgical device proximally while delivery the electrosurgical energy.

In certain aspects, prior to inserting the distal portion of the electrosurgical device into the fallopian tube, the method includes inserting the distal portion of the electrosurgical device into the fallopian tube utilizing a guide tube such that a distal end of the guide tube is disposed within the fallopian tube and sliding the electrosurgical device through the guide tube until the distal portion of the electrosurgical device extends from the guide tube.

In particular aspects, prior to applying suction the method includes expanding the fallopian tube about a flare of an end effector assembly to create an airtight seal therebetween.

In certain aspects, applying suction distal tip includes the tissue of the fallopian tube being drawn into the distal tip such that delivering electrosurgical energy includes the tissue of the fallopian tube being simultaneously drawn into and electorsurgically sealed adjacent the distal tip.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician.

Figure 1:
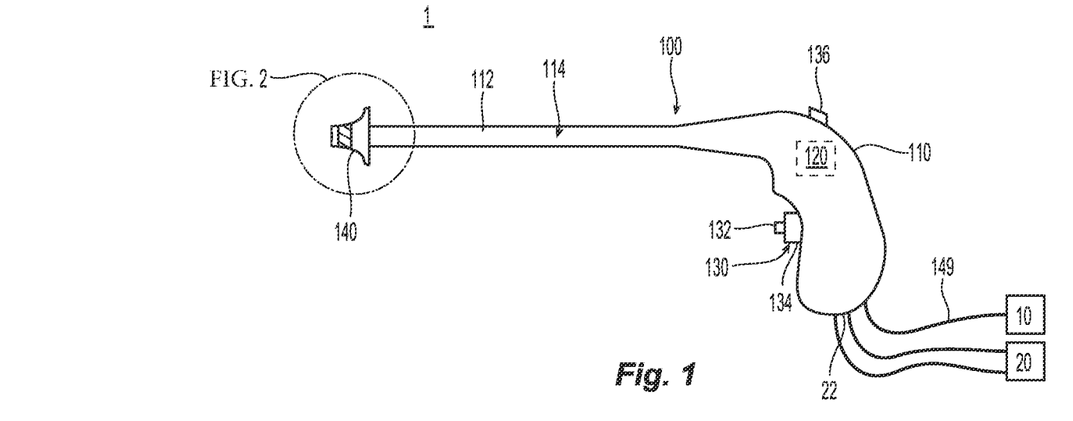
FIG. 1 is a side view of an exemplary electrosurgical system provided in accordance with the present disclosure including an electrosurgical device, an electrosurgical generator, and a vacuum source.

Referring now to FIG. 1, an electrosurgical system 1 is disclosed in accordance with the present disclosure and includes an electrosurgical generator 10, a vacuum source 20, and an electrosurgical device 100. The electrosurgical generator 10 is configured to provide electrosurgical energy to the electrosurgical device 100. As detailed herein, the electrosurgical energy is bipolar RF energy. Other types of energy are contemplated and may be utilized to accomplish the same or similar purpose, e.g., optical, microwave, ultrasonic, ultrasound, or thermal.

The vacuum source 20 is in communication with the electrosurgical device 100 and provides suction through one or more ports as detailed below. The vacuum source 20 may be external to the electrosurgical device 100 or may be disposed within a portion of the electrosurgical device 100 as shown as in phantom as vacuum source 120. In embodiments, the vacuum source 20, 120 is supplied with energy from the electrosurgical generator 10.

The electrosurgical device 100 includes a handle 110, an elongated body or shaft 112 extending from the handle 110, and an end effector 140 supported by a distal portion of the elongated shaft 112. The elongated shaft 112 may be flexible, semi-rigid, or rigid. In embodiments the elongated shaft 112 is curved along a longitudinal axis thereof to aid in insertion into a fallopian tube as detailed below. The elongated shaft 112 defines a suction channel 116 that is open at a distal tip 116 of the elongated shaft 112. The suction channel 116 may be defined by an outer wall of the elongated shaft 112. In embodiments, the suction channel 116 is defined by a tube that extends through the elongated shaft 112. The suction channel 116 is in communication with the vacuum source 20 connected to the handle 110. In embodiments, the vacuum source 20 may be releasably coupled to the handle 110 through a vacuum port 22. In particular embodiments, the vacuum source for the electrosurgical device 100 may be provided as a vacuum source 120 within the handle 110 with the suction channel 116 in communication with or terminating at the vacuum source 120. When the vacuum source 120 is disposed within the handle 110, the vacuum source 120 may be powered by a battery disposed within the handle 110, be powered by the electrosurgical generator 10, or be powered by a separate external power source (not shown).

Figure 2:
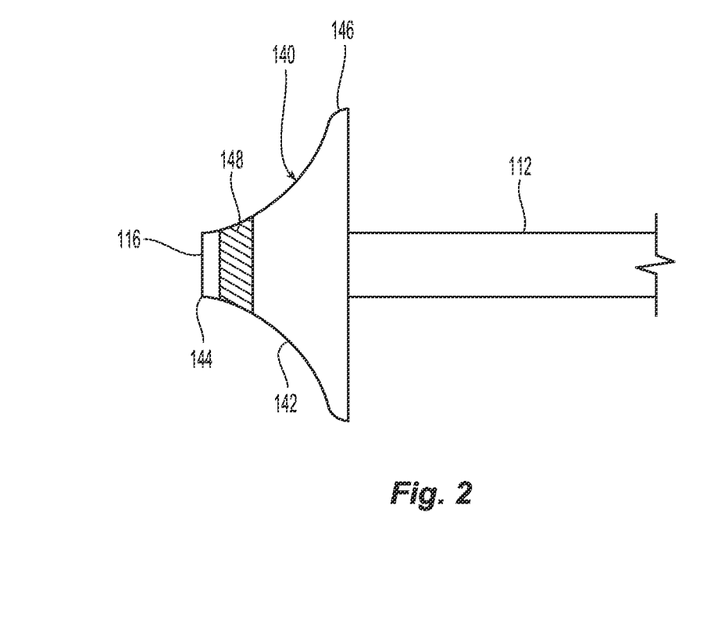
FIG. 2 is an enlarged view of a distal portion of the electrosurgical device of FIG. 1.
Figure 3:
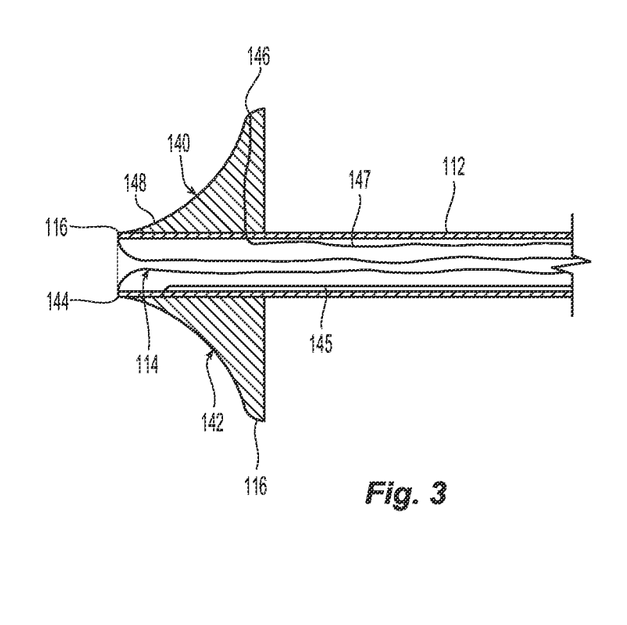
FIG. 3 is a cross-sectional side view of the distal portion of the electrosurgical device of FIG. 2.

With additional reference to FIGS. 2 and 3, the end effector 140 includes a flare 142 disposed about the elongated shaft 112. The flare 142 expands radially as it extends proximally from the distal tip 116 of the elongated shaft 112. The flare 142 includes a first or active electrode 144 and a second or return electrode 146 positioned proximal of the active electrode 144. The active electrode 144 is disposed adjacent the distal tip 116 of the elongated shaft 112. The return electrode 146 is positioned on an outer surface of the flare 142 and may be disposed at a proximal outer edge of the flare 142 that defines a distal end of the flare 142. Each of the active and return electrodes 144, 146 are in electrical communication with the electrosurgical generator 10. For example, the active and return electrodes 144, 146 may each be electrically coupled to the electrosurgical generator 10 by leads 145, 147 that extend through the elongated shaft 112 to the handle 110 of the electrosurgical device 100 and the electrosurgical generator 10 may be releasably coupled to the handle 110. The leads 145, 147 may be disposed within walls of the elongated shaft 112. In some embodiments, the electrosurgical device 100 includes a generator cable 149 that extends from the handle 110 to electrically connect the leads 145, 147 to the electrosurgical generator 10.

The end effector 140 includes an insulator 148 positioned on the flare 142 between the active electrode 144 and the return electrode 146. The insulator 148 insulates the active and return potentials from one another such that tissue is energized via the active electrode 144 and transferred through the tissue to the return electrode 146.

Referring back to FIG. 1, the handle 110 includes a control assembly 130 having one or more controls 132, 134, 136 for controlling the end effector 140. One of the controls is a vacuum control, e.g., control 136, that is operably connect to the vacuum source 20, 120 to control activation of suction from the vacuum source. Another of the controls is an energy control, e.g., control 134, that is operably connected to the electrosurgical generator 10 to control delivery of electrosurgical energy to the active electrode 144. In embodiments, the energy control may be a foot switch, e.g., foot switch 11 (FIG. 8), connected directly to the electrosurgical generator 10 or the handle 110 to control delivery of electrosurgical energy to the active electrode 144. In some embodiments, the vacuum control and the energy control function as a two-stage switch such that initial activation activates suction and subsequent activation activates delivery of electrosurgical energy. For example, a control 132 may be stacked on control 134 such that an initial pressing of control 132 activates suction as the control 132 is depressed into control 134 and additional pressing of control 132 depresses control 134 towards the handle 110 to activate delivery of electrosurgical energy. Alternatively, the order of movement of the controls may be reversed such that initial pressing of the control 132 moves both control 132 and control 134 towards the handle 110 to activate suction and subsequent pressing of the control 132 moves control 132 into control 134 to activate delivery of electrosurgical energy.

Figure 4:
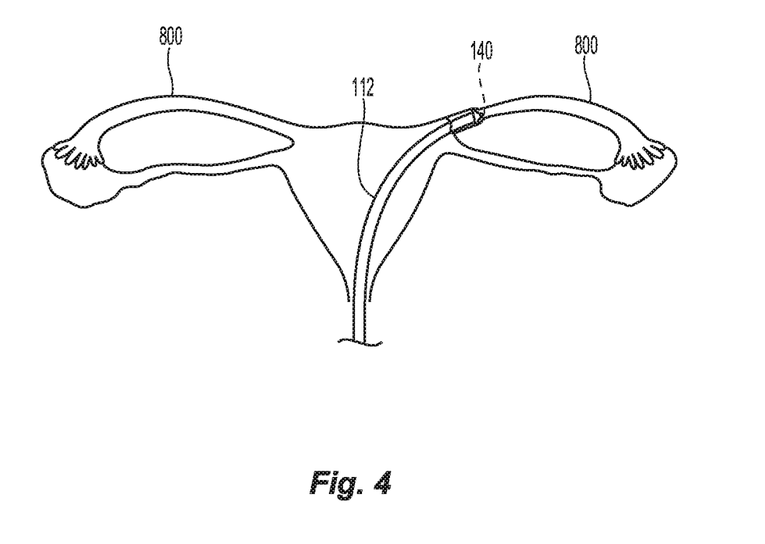
FIG. 4 is a schematic representation of a uterus of a patient with a portion of the electrosurgical device of FIG. 1 positioned within a fallopian tube of the uterus.

With reference now to FIGS. 4-7, a method of sealing a fallopian tube with the electrosurgical device 100 will be detailed with reference to the electrosurgical system 1 of FIGS. 1-3. Initially, the end effector 140 of the electrosurgical device 100 is inserted into a fallopian tube 800 through a hysteroscopic approach, as shown in FIG. 4, such that the end effector 140 is disposed within a fallopian tube 800 to be sealed. The elongated shaft 112 may be curved to aid in insertion into the fallopian tube 800. In embodiments, the elongated shaft 112 is semi-rigid or flexible allowing the elongated shaft 112 to adjust to an anatomy of the patient for insertion into the fallopian tube 800.

Figure 5:
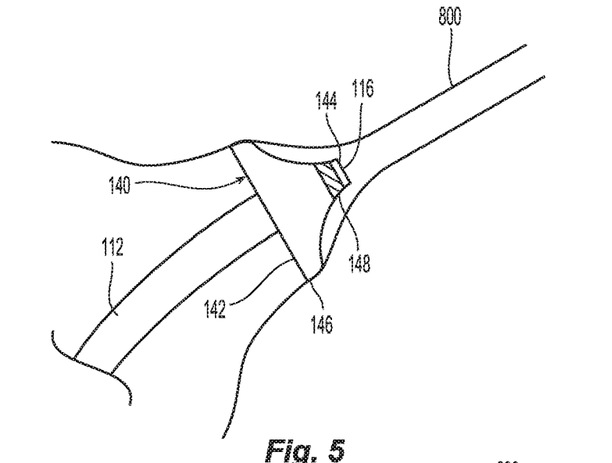
FIG. 5 is an enlarged view of the portion of the uterus illustrating the electrosurgical device within the fallopian tube of FIG. 4.
Figure 6:
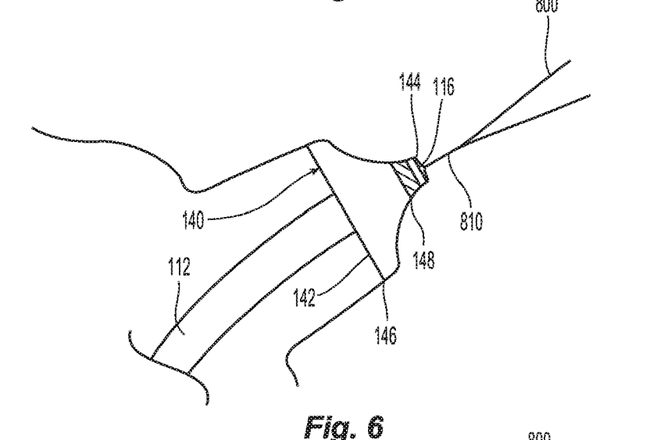
FIG. 6 is the enlarged view of the portion of the uterus of FIG. 4 with the electrosurgical device applying suction and electrosurgical energy to the fallopian tube.

Referring now to FIG. 5, as the end effector 140 is inserted into the fallopian tube 800, the flare 142 may expand the fallopian tube 800 about the end effector 140 and form a substantially airtight seal within the fallopian tube 800. When the end effector 140 is disposed within the fallopian tube 800 such that a substantially airtight seal is formed, the vacuum source 20, or 120, is activated to apply suction through the channel 114 of the elongated shaft 112. The suction collapses the fallopian tube 800 about the end effector 140 such that the fallopian tube 800 is closed at the tip 116 of the elongated shaft 112 as shown in FIG. 6. The suction is sufficient to overcome air which may seep through the air tight seal formed by the flare 142 but not enough to tear the walls of the fallopian tube 800. The suction may draw a portion of the fallopian tube 800 into the distal tip 116 and within the channel 114.

With the fallopian tube 800 collapsed at or within the distal tip 116, the electrosurgical generator 10 is activated such that electrosurgical energy is provided to the active electrode 144. The electrosurgical energy flows from the active electrode 144 through the collapsed fallopian tube 800 and to the return electrode 146 such that a seal 810 is formed in the fallopian tube 800 at the tip 116 of the elongated shaft 112. The insulator 148, positioned on the flare 142, directs or shapes the flow of energy from the active electrode 144 through tissue of the fallopian tube 800 to improve the seal 810.

When the seal 810 is formed, the electrosurgical generator 10 is deactivated and the vacuum source 20, or 120, is deactivated. The electrosurgical generator 10 may be deactivated in advance of deactivating the vacuum source 20, 120 or the electrosurgical generator 10 and vacuum source 20, 120 may be deactivated simultaneously.

Figure 7:
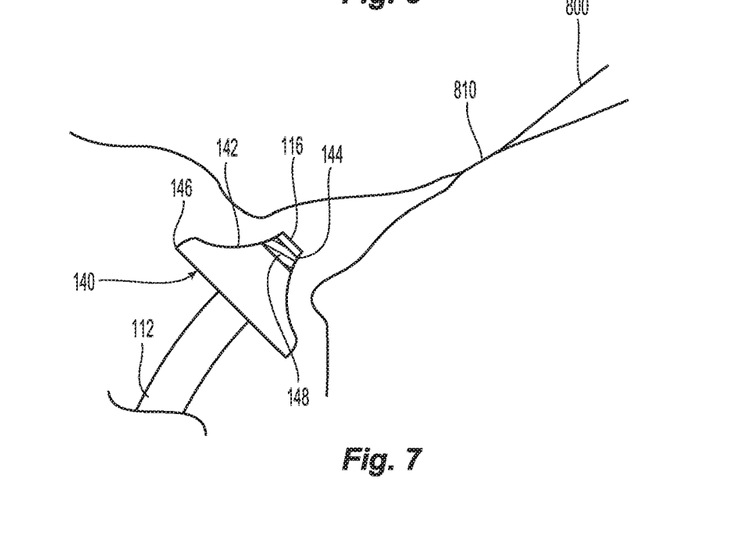
FIG. 7 is the enlarged view of the portion of the uterus of FIG. 4 with the portion of the electrosurgical device shown withdrawn from the fallopian tube.

When the electrosurgical generator 10 and the vacuum source 20, 120 are deactivated, the end effector 140 is withdrawn from the fallopian tube 800 leaving the seal 810 as shown in FIG. 7. The end effector 140 may be used to seal the other fallopian tube 800 or be removed from the patient.

The method of sealing a fallopian tube 800 detailed above may be performed in a medical office without requiring general anesthesia and may be completed without leaving implanted or foreign materials within the patient. Further, the method of sealing a fallopian tube 800 detailed above forms an immediate and permanent seal of the fallopian tube 800 which may reduce the time of a surgical procedure, reduce the cost of a surgical procedure, and improve patient outcomes associated with sealing fallopian tubes.

Figure 8:
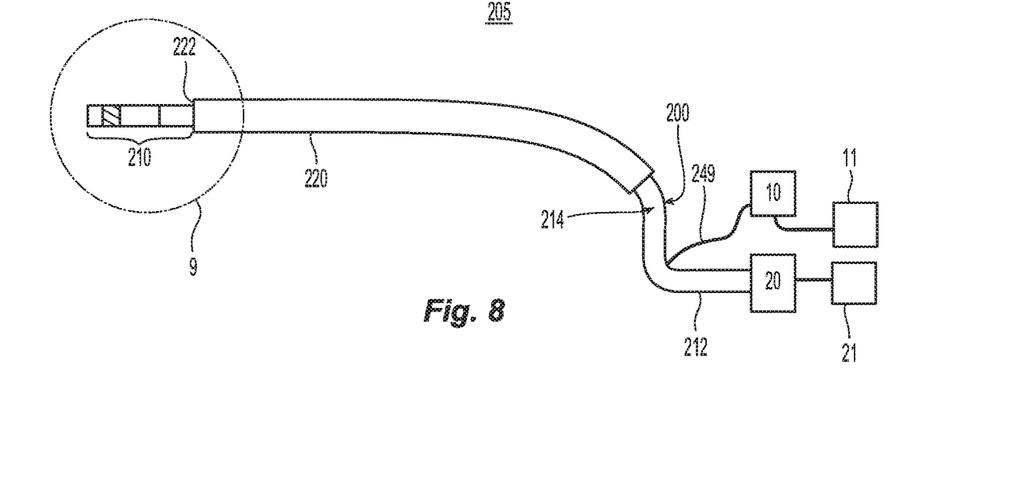
FIG. 8 is a side view of another exemplary electrosurgical system provided in accordance with the present disclosure including a guide tube, an electrosurgical device, an electrosurgical generator, and a vacuum source.

With reference to FIG. 8, another electrosurgical system 205 is disclosed in accordance with the present disclosure. The electrosurgical system 205 includes the electrosurgical generator 10, the vacuum source 20, an electrosurgical device 200, and a guide tube 220. The guide tube 220 is a rigid or semi-rigid tube that is inserted through a hysteroscopic approach to position a distal end 222 of the guide tube 220 within a fallopian tube and guide the electrosurgical device 200 into the fallopian tube, as detailed below. The electrosurgical generator 10 may include a foot pedal 11 and the vacuum source 20 may include a foot pedal 21 to activate the respective one of the electrosurgical generator 10 or the vacuum source 20. In embodiments, a single two-stage foot pedal (not shown) may be used to activate the vacuum source 20 at a first stage and the electrosurgical generator 10 with the vacuum source 20 at a second stage.

Figure 9:
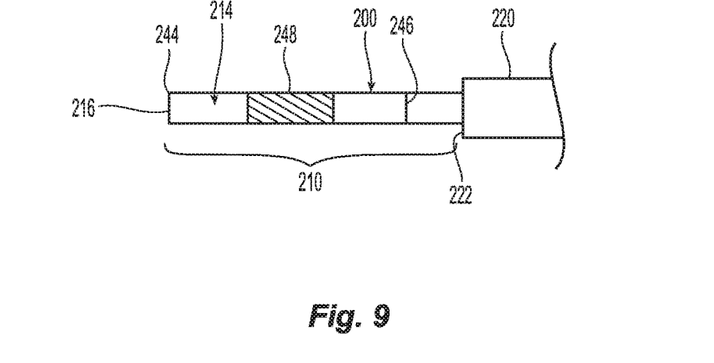
FIG. 9 is an enlarged view if the indicated area of detail of FIG. 8.
Figure 10:
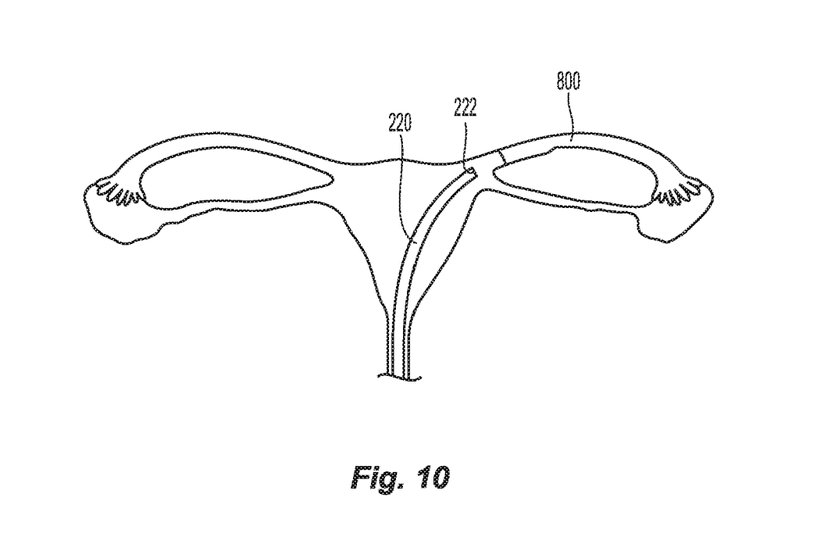
FIG. 10 is a schematic representation of a uterus of a patient with a distal end of the guide tube of FIG. 8 positioned within a fallopian tube of the uterus.

With additional reference to FIG. 9, the electrosurgical device 200 is in the form of a catheter 200 having an elongated body or shaft that is flexible and includes a distal portion 210, a proximal portion 212, and a channel 214 defined therethrough. The distal portion 210 is configured to extend from the distal end 222 of the guide tube 220 and to act as an end effector of the electrosurgical device 200 to deliver suction and electrosurgical energy to tissue beyond the distal end 222 of the guide tube 220 as detailed below. The proximal portion 212 includes channel 214 defined therethrough that is in communication with the vacuum source 20 such that when the vacuum source 20 is activated, suction is provided through the distal tip 216 of the electrosurgical device 200.

The distal portion 210 includes an active electrode 244, a return electrode 246, and an insulator 248. The active electrode 244 is positioned adjacent the distal tip 216 of the catheter 200 in electrical communication with the electrosurgical generator 10. The active electrode 244 may be positioned on the distal tip 216 or may be positioned on an outer surface of the distal portion 210 at the distal tip 216. The return electrode 246 is positioned on an outer surface of the distal portion 210 proximal of the active electrode 244 and is in electrical communication with the electrosurgical generator 10. The insulator 248 is disposed about the outer surface of the distal portion 210 between the active and return electrodes 244, 246. The insulator 248 insulates the active and return potentials from one another such that tissue is energized via the active electrode 244 and transferred through the tissue to the return electrode 246 as detailed below.

With reference now to FIGS. 10-13, a method of sealing a fallopian tube with the electrosurgical device 200 will be detailed with reference to the electrosurgical system 205 of FIGS. 8 and 9. Initially referring to FIG. 10, the guide tube 220 is inserted into a fallopian tube 800 through a hysteroscopic approach such that the distal end 222 of the guide tube 220 is positioned within the fallopian tube 800 to be sealed.

Figure 11:
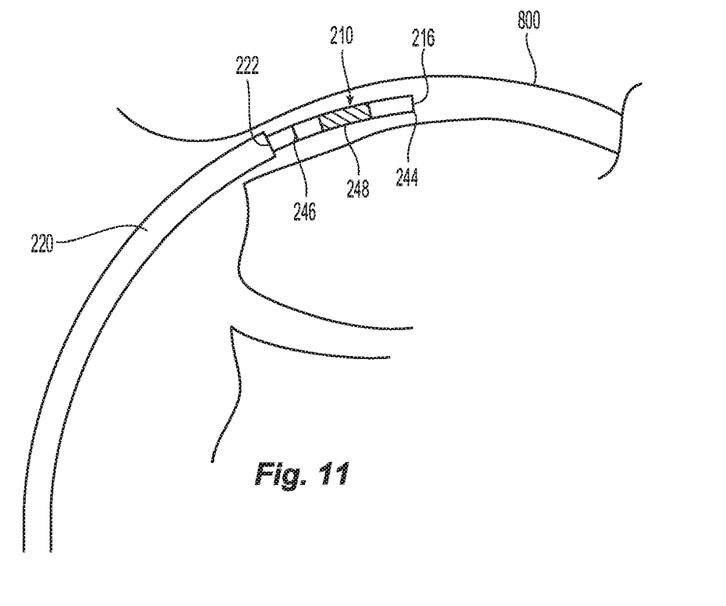
FIG. 11 is an enlarged view of the portion of the uterus illustrating the distal end of the guide tube of FIG. 10 positioned within the fallopian tube with a distal portion of the electrosurgical device of FIG. 8 extending from the distal end of the guide tube.

With particular reference to FIG. 11, with the distal end 222 positioned within the fallopian tube 800, the electrosurgical device 200 is inserted through guide tube 220 until the distal portion 210 of the electrosurgical device 200 extends from the distal end 222 of the guide tube 220 into the fallopian tube 800. The electrosurgical device 200 may be extended until the return electrode 246 is positioned beyond the distal end 222. In certain embodiments, the electrosurgical device 200 is extended over the guide tube 220 such that the guide tube 220 is disposed within the electrosurgical device 200. In embodiments, the distal portion 210 of the electrosurgical device 200 may be positioned in the fallopian tube 800 without the use of the guide tube 220. In some embodiments, a guide wire (not shown) may be used to position the distal portion 210 of the electrosurgical device 200 within the fallopian tube 800 instead of the guide tube 220. Once the distal portion 210 of the electrosurgical device 200 is positioned within the fallopian tube 800, the guide tube 220 may remain within or may be removed from the patient for the remainder of the procedure.

Figure 12:
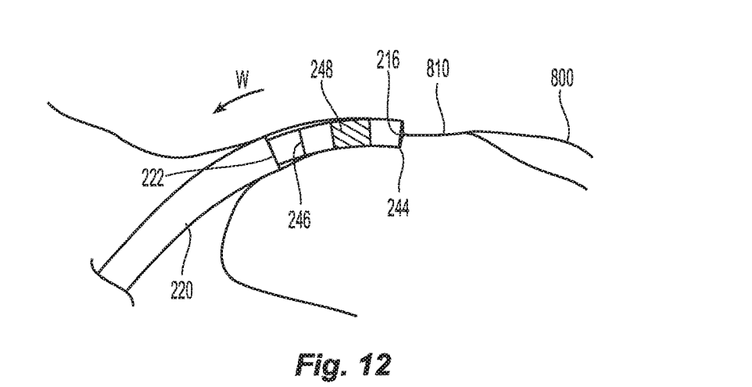
FIG. 12 is the enlarged view of the portion of the uterus of FIG. 10 with the electrosurgical device applying suction and electrosurgical energy to the fallopian tube.
Figure 13:
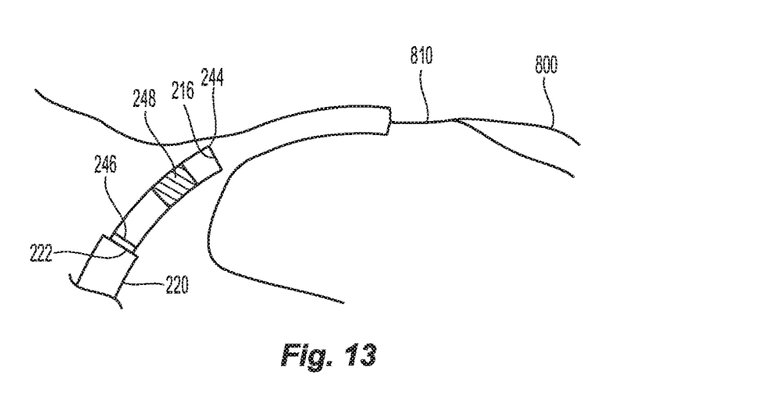
FIG. 13 is the enlarged view of the portion of the uterus of FIG. 10 with the distal portion of the electrosurgical device shown withdrawn from the fallopian tube.

With the distal portion 210 positioned within the fallopian tube 800, the vacuum source 20 is activated to apply suction from the distal end 216 to collapse or close the fallopian tube 800 beyond or at the distal end 216 as shown in FIG. 12. The vacuum source 20 may be activated by depressing the foot pedal 21. The electrosurgical generator 10 is activated when the vacuum source 20 is applying suction through the electrosurgical device 200 such that electrosurgical energy is delivered to tissue, e.g., the fallopian tube 800, by the active electrode 244 and is returned to the electrosurgical generator 10 via the return electrode 246. As electrosurgical energy is delivered by the electrosurgical generator 10, the electrosurgical device 200 is withdrawn in the direction indicated by arrow W in FIG. 12 to form a seal 810. The position of the insulator 248 insulates the active and return potentials from one another such that tissue is energized with electrosurgical energy to form the seal 810 in the fallopian tube 800 at or beyond the distal end 216 as the distal portion 210 is withdrawn. When the seal 810 has sufficient length, the electrosurgical generator 10 is deactivated and the vacuum source 20 is deactivated while the electrosurgical device 200 is fully withdrawn from the fallopian tube 800 leaving the seal 810 within the fallopian tube 800 as shown in FIG. 13. The electrosurgical generator 10 may be deactivated in advance of deactivating the vacuum source 20 or the electrosurgical generator 10 and vacuum source 20, or 120, may be deactivated simultaneously. The return electrode 246 may be disposed within the guide tube 200 while electrosurgical energy is being delivered by the active electrode 244. The electrosurgical device 200 may be used to seal the other fallopian tube 800 or removed from the patient after the seal 810 is formed.

The method of sealing a fallopian tube 800 detailed above may be performed in a medical office without requiring general anesthesia and may be completed without leaving implanted or foreign materials within the patient. Further, the method of sealing a fallopian tube 800 detailed above forms an immediate and permanent seal of the fallopian tube 800 which may reduce the time of a surgical procedure, reduce the cost, and improve patient outcomes associated with sealing fallopian tubes.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An electrosurgical device, comprising:
an elongated shaft defining a longitudinal axis, the elongated shaft having an end effector operably engaged with a distal portion of the elongated shaft and a channel defined through the elongated shaft, the end effector including a distal tip and configured to provide suction from a suction source to the distal tip through the channel, the end effector having a distal outer periphery disposed about the longitudinal axis, the distal outer periphery extending a first radial distance from the longitudinal axis, the end effector including a flare at a proximal end of the end effector, the flare having a proximal outer periphery, the proximal outer periphery having a second radial distance from the longitudinal axis, the second radial distance being larger than the first radial distance;
an active electrode positioned adjacent the distal tip of the elongated shaft and configured to deliver electrosurgical energy to tissue; and
a return electrode positioned on an outer surface of the flare of the end effector proximal of the active electrode, the return electrode configured to provide a return path for the electrosurgical energy.

2. The electrosurgical device according to claim 1, further comprising an insulator disposed about the elongated shaft between the active and return electrodes.

3. The electrosurgical device according to claim 1, wherein the flare radially expands as the flare extends proximally from the distal tip of the elongated shaft.

4. The electrosurgical device according to claim 3, wherein the return electrode is disposed on a proximal outer edge of the flare.

5. The electrosurgical device according to claim 1, further comprising a handle operably engaged to a proximal portion of the elongated shaft.

6. The electrosurgical device according to claim 5, wherein the handle includes a vacuum source disposed therein, the vacuum source in communication with the channel of the elongated shaft and configured to provide suction through the distal tip of the elongated shaft.

7. The electrosurgical device according to claim 1, wherein the elongated shaft is flexible.

8. The electrosurgical device according to claim 1, wherein the channel of the elongated shaft is curved between a proximal portion and the distal portion of the elongated shaft.

9. An electrosurgical system, comprising:
an electrosurgical device including:
an elongated shaft having a distal portion and a channel defined through the elongated shaft, the distal portion having a distal tip and curving outwardly in a proximal direction to define a concavity;
an active electrode positioned adjacent the distal tip of the elongated shaft, the active electrode configured to deliver electrosurgical energy to tissue; and
a return electrode positioned on an outer surface of the distal portion of the elongated shaft proximal of the active electrode, the return electrode configured to provide a return path for the electrosurgical energy;
a vacuum source in communication with the channel and configured to provide suction to the distal tip of the elongated shaft; and
an electrosurgical generator in electrical communication with the active electrode and the return electrode.

10. The electrosurgical system according to claim 9, further comprising:
a first control in communication with the vacuum source and configured to control activation of the vacuum source; and
a second control in communication with the electrosurgical generator and configured to control activation of the electrosurgical generator.

11. The electrosurgical system according to claim 10, wherein the first and second controls are operably engaged to one another as a single two-stage switch.

12. The electrosurgical system according to claim 10, wherein the electrosurgical device includes a handle operably engaged with a proximal portion of the elongated shaft, at least one of the first or second controls disposed on the handle.

13. The electrosurgical system according to claim 10, wherein at least one of the first or second controls is a foot pedal.

14. The electrosurgical system according to claim 9, further comprising a guide tube having a channel defined therethrough and distal end configured to position the electrosurgical device within a patient.

15. The electrosurgical system of claim 9, wherein an outer surface of the distal portion has a distal diameter and a proximal diameter, and wherein the proximal diameter is larger than the distal diameter.

16. The electrosurgical system of claim 9, wherein the elongated shaft defines a longitudinal axis, and wherein the channel is coaxial with the longitudinal axis.

* * * * *